United States Patent
Kadobayashi et al.

(10) Patent No.: US 9,847,030 B2
(45) Date of Patent: Dec. 19, 2017

(54) DISPATCH OF AUTOMATED EXTERNAL DEFIBRILLATORS

(71) Applicant: EMPIRE TECHNOLOGY DEVELOPMENT LLC, Wilmington, DE (US)

(72) Inventors: Rieko Kadobayashi, Kyoto (JP); Tsutomu Miyasato, Nara (JP); Noriaki Kuwahara, Nara (JP); Masataka Ohira, Saitama (JP); Noriaki Mitsunaga, Osaka (JP)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 14/917,278

(22) PCT Filed: Nov. 13, 2013

(86) PCT No.: PCT/US2013/069883
§ 371 (c)(1),
(2) Date: Mar. 8, 2016

(87) PCT Pub. No.: WO2015/072984
PCT Pub. Date: May 21, 2015

(65) Prior Publication Data
US 2016/0217691 A1 Jul. 28, 2016

(51) Int. Cl.
*H04W 4/02* (2009.01)
*G08G 1/00* (2006.01)
(Continued)

(52) U.S. Cl.
CPC .......... *G08G 1/202* (2013.01); *A61N 1/3993* (2013.01); *G01S 19/51* (2013.01); *G06Q 10/083* (2013.01);
(Continued)

(58) Field of Classification Search
CPC .... G08B 25/016; H04W 4/22; H04W 76/007; H04W 4/02
See application file for complete search history.

(56) References Cited

U.S. PATENT DOCUMENTS

| | | |
|---|---|---|
| 4,109,985 A | 8/1978 | Lieb, Jr. |
| 6,986,463 B2 | 1/2006 | Ludtke |

(Continued)

FOREIGN PATENT DOCUMENTS

| | | |
|---|---|---|
| JP | 2008229091 A | 10/2008 |
| JP | 2009517682 A | 4/2009 |

(Continued)

OTHER PUBLICATIONS

"AED installation Site Search," accessed at https://web.archive.org/web/20131031134230/http://www.qqzaidan.jp/AED/aed.htm, posted on Oct. 21, 2013, p. 1 (Machine Translation).

(Continued)

*Primary Examiner* — Wesley Kim
*Assistant Examiner* — Dong-Chang Shiue
(74) *Attorney, Agent, or Firm* — Turk IP Law, LLC

(57) ABSTRACT

Technologies are generally described for an automated external defibrillator (AED) dispatch system. In various examples, the AED dispatch system may include a receiver, a vehicle determination unit, and a transmitter. The receiver may be configured to receive, from a first device, a request message that includes first location information that indicates a location of the first device, and also receive, from one or more of second devices, one or more report messages, each of which includes second location information that indicates a location of the corresponding one of the second devices. The vehicle determination unit may be configured to select a vehicle to be dispatched based at least in part on the first location information and the respective second (Continued)

location information. The transmitter may be configured to transmit an instruction message to the second device associated with the selected vehicle to be dispatched.

21 Claims, 7 Drawing Sheets

(51) Int. Cl.
  *G06Q 50/22* (2012.01)
  *G06Q 10/08* (2012.01)
  *A61N 1/39* (2006.01)
  *G01S 19/51* (2010.01)
  *G08G 1/005* (2006.01)
  *G08G 1/13* (2006.01)
(52) U.S. Cl.
  CPC ............ *G06Q 50/22* (2013.01); *G08G 1/005* (2013.01); *G08G 1/13* (2013.01)

(56) References Cited

U.S. PATENT DOCUMENTS

| | | | |
|---|---|---|---|
| 7,289,029 | B2 | 10/2007 | Medema et al. |
| 7,430,340 | B2 | 9/2008 | Glass et al. |
| 7,924,149 | B2 | 4/2011 | Mendelson |
| 8,314,683 | B2 * | 11/2012 | Pfeffer ................. G08B 25/006 340/539.13 |
| 2007/0043585 | A1 | 2/2007 | Matos |
| 2010/0017471 | A1 | 1/2010 | Brown et al. |
| 2010/0163431 | A1 | 7/2010 | Laitenberger et al. |
| 2011/0060378 | A1 * | 3/2011 | Tuysserkani ......... A61B 5/0022 607/5 |
| 2011/0099040 | A1 * | 4/2011 | Felt ..................... G06F 17/3087 705/7.12 |
| 2012/0041278 | A1 * | 2/2012 | Sadhu ................. A61B 5/0006 600/301 |
| 2015/0079932 | A1 * | 3/2015 | Zelinka ................. H04W 12/02 455/411 |

FOREIGN PATENT DOCUMENTS

| | | | |
|---|---|---|---|
| JP | 2013114430 | A * | 6/2013 |
| KR | 100606783 | B1 | 8/2006 |
| WO | 2008149467 | A1 | 12/2008 |

OTHER PUBLICATIONS

"Requirements Specification Ambulance Dispatch System," Delivarable 2, Advanced Software Engineering Course Project, pp. 1-29, accessed on Feb. 12, 2016.

International Search Report and Written Opinion for International Application No. PCT/US2013/069883, dated Aug. 7, 2014.

"About AEDs," accessed at http://web.archive.org/web/20130713082621/http://www.defibtech.com/support/about-aeds, accessed on Dec. 12, 2016, p. 1.

Sherrif, C., "AED Equipped Patrol Cars," accessed at https://www.youtube.com/watch?v=LIJUJJShSlU, Uploaded on Jun. 1, 2010, pp. 3.

* cited by examiner

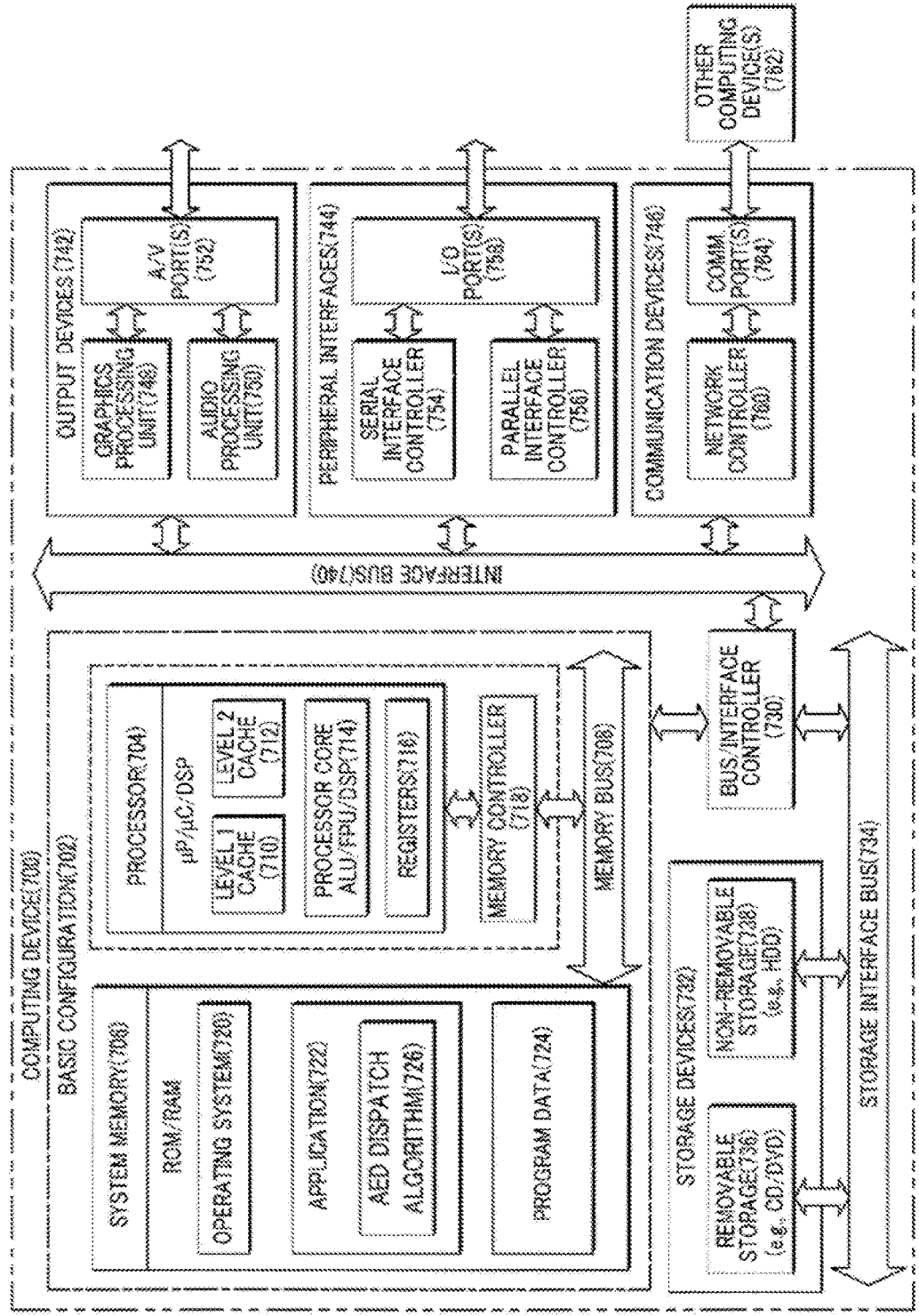

DISPATCH OF AUTOMATED EXTERNAL DEFIBRILLATORS

CROSS-REFERENCE TO RELATED APPLICATION

This Application is the U.S. National Stage filing under 35 U.S.C. §371 of International Application No. PCT/US13/69883 filed on Nov. 13, 2013. The International Application is herein incorporated by reference in its entirety.

BACKGROUND

Unless otherwise indicated herein, the approaches described in this section are not prior art to the claims in this application and are not admitted to be prior art by inclusion in this section.

An automated external defibrillator (AED) is a portable electronic device that analyzes a cardiac rhythm of a patient and, if appropriate, advises and/or delivers electrical therapy to the patient. The AED is used in a case of potentially life threatening cardiac arrhythmia, which may lead to a cardiac arrest. Specifically, the AED is able to automatically diagnose the cardiac arrhythmia of ventricular fibrillation and/or ventricular tachycardia in the patient, and treat them through defibrillation. The application of the electrical therapy allows the heart of the patient to reestablish an effective rhythm.

The cardiac arrhythmia may rapidly lead to irreversible brain damage and death without being successfully treated by defibrillation. It is known that for every minute that a person in cardiac arrest goes without being successfully treated by defibrillation, the chance of survival decreases by 7 percent per minute in the first 3 minutes, and decreases by 10 percent per minute as time advances beyond 3 minutes.

SUMMARY

Technologies are generally described for dispatch of automated external defibrillators (AEDs), including systems, methods, and apparatus related to AED dispatch.

Various example automated external defibrillator (AED) dispatch systems described herein may include a receiver, a vehicle determination unit and a transmitter. The receiver may be configured to receive, from a first device, a request message which may include first location information indicating a location of the first device. The receiver may also be configured to receive, from one or more of multiple second devices, one or more report messages, each of which may include second location information indicating a location of the corresponding one of the second devices. Each second device may be associated with each of multiple candidate vehicles, and each candidate vehicle may have an automated external defibrillator (AED). The vehicle determination unit may be configured to select a vehicle to be dispatched from among the multiple candidate vehicles based at least in part on the first location information and the respective second location information. The transmitter may be configured to transmit an instruction message that may include the first location information to the second device associated with the selected vehicle to be dispatched.

In some examples, a method for an automated external defibrillator (AED) dispatch system is described, such as any example method described herein, that may be performed under control of any automated external defibrillator (AED) dispatch system described herein. Some methods may include receiving a request message from a first device, and receiving one or more report messages from one or more of multiple second devices. The request message may include first location information to indicate a location of the first device, and each report message may include second location information to indicate a location of the corresponding one of the second devices. Each second device may be associated with each of multiple candidate vehicles, and each candidate vehicle may have an automated external defibrillator (AED). Some methods may further include determining a vehicle to be dispatched from among the multiple candidate vehicles based at least in part on the first location information and the respective second location information. Various methods may further include transmitting an instruction message that may include the first location information to the second device associated with the determined vehicle to be dispatched.

In some examples, an automated external defibrillator (AED) is described, such as any example automated external defibrillator (AED) described herein, that may be adapted to utilize a defibrillation unit, a location identification unit and a wireless communications unit. Various defibrillation units may be configured to provide a patient with electrical therapy. The location identification unit may be configured to identify location information of the automated external defibrillator (AED). The wireless communications unit may be configured to transmit the identified location information to an associated device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 7 is a block diagram illustrating an example computing device that may be utilized to implement dispatch of an automated external defibrillator (AED), all arranged in accordance with at least some embodiments described herein.

DETAILED DESCRIPTION

Figure 1:
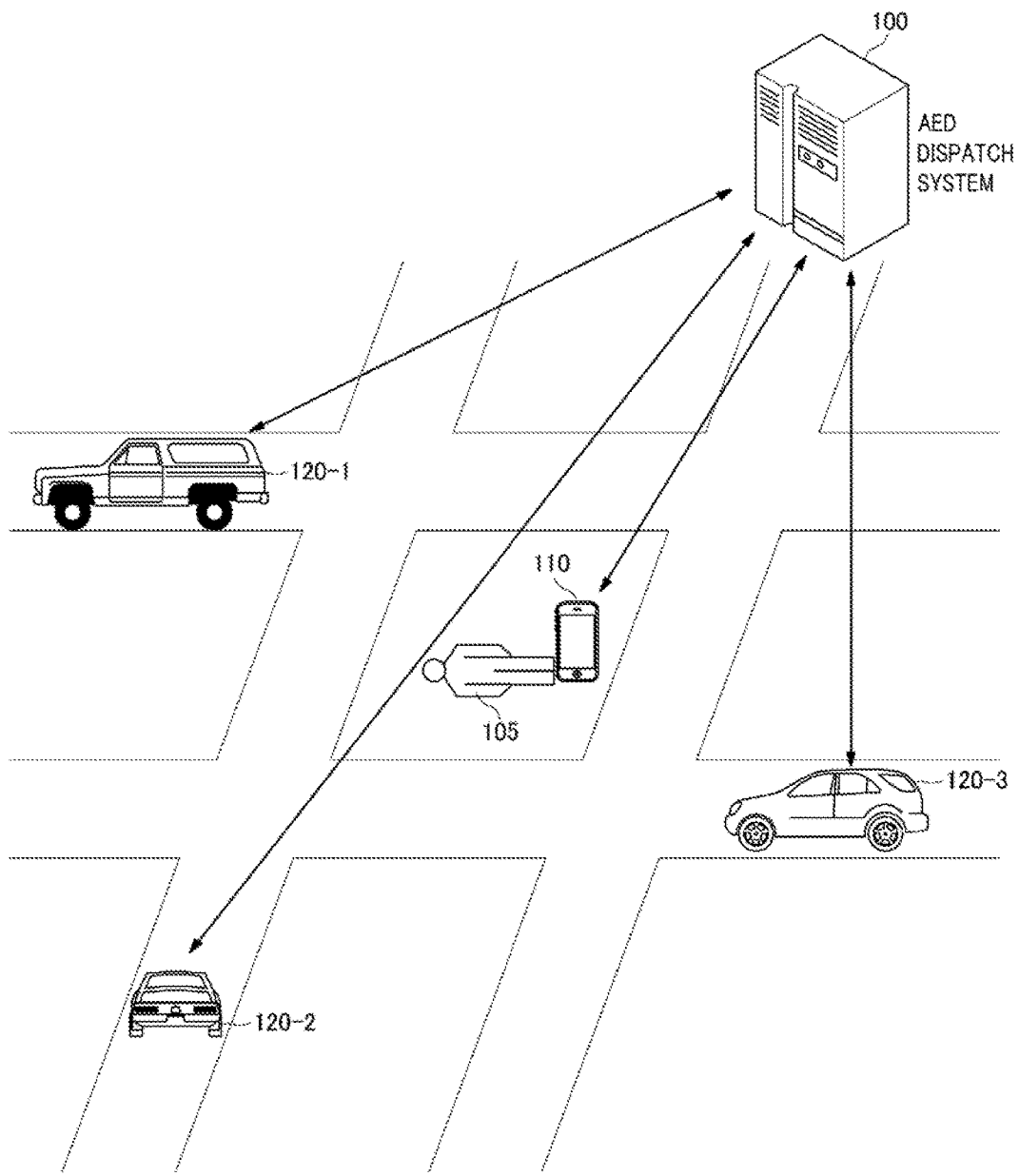
FIG. 1 schematically shows an illustrative example environment in which an automated external defibrillator (AED) dispatch system may dispatch a vehicle carrying an automated external defibrillator (AED) to a patient.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, may be arranged, substituted, combined, separated, and designed in a wide variety of different configurations, all of which are explicitly contemplated herein.

This disclosure is generally drawn, inter alia, to methods, apparatus, systems, devices and computer program products related to a defibrillator dispatch system, such as an automated external defibrillator (AED) dispatch system.

Briefly stated, technologies are generally described relating to a defibrillator dispatch system, which may be utilized to dispatch one or more vehicles carrying a defibrillator to a patient location based on the location of the patient relative to the one or more vehicles. In various examples, the AED dispatch system may include a receiver, a vehicle determination unit, and a transmitter. The receiver may be configured to receive, from a first device, a request message that includes first location information that indicates a location of the first device, and also receive, from one or more of second devices, one or more report messages, each of which includes second location information that indicates a location of the corresponding one of the second devices. The vehicle determination unit may be configured to select a vehicle to be dispatched based at least in part on the first location information and the respective second location information. The transmitter may be configured to transmit an instruction message to the second device associated with the selected vehicle to be dispatched.

Some examples of an automated external defibrillator (AED) dispatch system are configured to dispatch a vehicle carrying an automated external defibrillator (AED) to a patient location based on the location of the patient relative to the vehicle.

The patient may be in possession of a first device, the first device being operable to provide location information associated with the person. Location information may be provided continuously, at intervals, or after a triggering event, such as a medical incident (e.g., a medical incident may be detected automatically or following a patient input through an input interface of the first device). For example, a patient aware of concerning medical symptoms may initiate a trigger event through interaction with the first device, after which location information may be provided more frequently, or effectively continuously, for a predetermined time. For example, a person may subscribe to a service, and as part of the subscription, a device is provided or configured to provide location information. In some examples, pressing an emergency button on the first device will both send location information to the defibrillator dispatch system and make contact with 911 or equivalent emergency services. Location information may be sent as part of a request message, the request message requesting dispatch of a defibrillator.

Location information associated with the patient (sometimes termed first location information or patient location information) may be provided by a first device, such as one carried, affixed, or otherwise associated with the patient. In some examples, the first device may be a multi-functional device, such as a portable electronic device (PED) having one or more additional functional capabilities, such as one or more of the functionalities of a phone, computer, personal digital assistant (PDA), global positioning system (GPS), camera, medical monitoring device (such as an electrocardiogram), digital voice recorder, identity card (such as an identity badge, drivers' license, and the like) and the like. In urban areas, where GPS signals may be lost, an alternative positioning system may be used as a backup, for example using phone network information.

In some examples, the first device is configured to be in communication (e.g., wired or wireless communication) with one or more physiological monitors, which may provide monitor signals indicative of a medical emergency such as a heart problem. For example, a phone type of device may be configured to provide the location information may be in wireless (e.g., Bluetooth) communication with a separate physiological monitor, such as a heart monitor. An example physiological monitor may include skin-contacting electrodes and an electronic circuit configured to detect and analyze electrical signals originating from heart activity. In some examples, the first device may be a physiological monitor configured with wireless network access.

In various examples, the AED dispatch system may receive a request message from a first device associated with the patient. The first device may be a device of the patient, or a device located within proximity of the patient, where examples of the first device may include a smartphone, a cellular phone, a tablet computer, a personal data assistant (PDA), a laptop computer, a desktop computer, or the like. The AED dispatch system may also receive one or more report messages from second devices, (e.g., periodically received messages). The second devices may be respectively associated with multiple candidate vehicles, each of which may have or carry the AED. By way of example, but not limitation, the second device may be embedded in the AED. By way of another example, but not limitation, the second device may be an electronic device mounted on the corresponding vehicle equipped with the AED, such as a navigation device of the vehicle. By way of yet another example, but not limitation, the second device may be an electronic device that may be operated by a driver of the corresponding vehicle equipped with the AED, where the second device may be a smartphone, a cellular phone, a tablet computer, a personal data assistant (PDA), or the like.

In some embodiments, the request message may include first location information that may indicate a location of the first device, and each of the report messages may include second location information that may indicate a location of the corresponding one of the second devices. The AED dispatch system may then select a vehicle to be dispatched from among the multiple candidate vehicles that are each equipped with the AED, based at least in part on the location of the first device and the locations of the second devices. The AED dispatch system may be configured to select one or more vehicles to dispatch based on consideration of which vehicle, among the multiple candidate vehicles, is able to reach the patient most rapidly. By way of example, but not limitation, the AED dispatch system may be configured to select the vehicle to be dispatched further based on locations of the respective candidate vehicles, and/or traffic conditions between the patient and the respective candidate vehicles.

In some embodiments, responsive to the request message, the AED dispatch system may be configured to generate an instruction message that may include the location of the first device (e.g., the location of the patient), and transmit the generated instruction message to the second device associated with the selected vehicle to be dispatched. By way of example, but not limitation, the instruction message may further include route information for the vehicle to be dispatched to reach the patient.

FIG. 1 schematically shows an illustrative example environment in which an automated external defibrillator (AED) dispatch system may dispatch a vehicle carrying an automated external defibrillator (AED) to a patient, arranged in accordance with at least some embodiments described herein. As illustrated, FIG. 1 shows an AED dispatch system 100, a patient 105, a first device 110, a first vehicle 120-1, a second vehicle 120-2, and a third vehicle 120-3. The patient is associated with the first device. The first device is arranged in communication with the AED dispatch system, and may send request messages to the AED dispatch system when assistance is needed. The AED dispatch system is arranged in communication with the first device, and also with vehicle occupants (such as the vehicle operator) of candidate vehicles (such as first, second, and third vehicles) through second devices associated with the vehicles or occupants thereof.

During operation, a patient 105 who may need an AED and/or anyone around patient 105, may manipulate first device 110 to send a request message to AED dispatch system 100. Examples of device 110 may include, but are not limited to, a smartphone, a cellular phone, a tablet computer, a personal data assistant (PDA), a laptop computer, vehicle electronics, a desktop computer, etc.

In some embodiments, the request message may include first location information that may indicate a location of the first device 110. By way of example, but not limitation, the first location information may include GPS (Global Positioning System) coordinates of the first device 110, cell information of a cellular network accessed by the first device 110, and/or information associated with a Wi-Fi access point accessed by the first device 110.

Figure 2A:
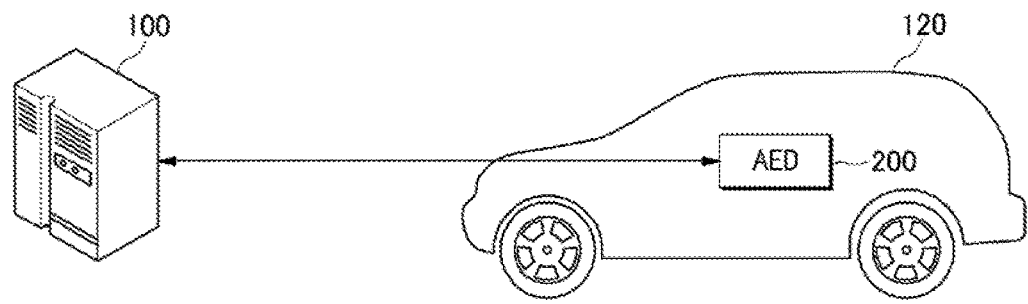
FIG. 2A schematically shows an illustrative example of interaction between an automated external defibrillator (AED) dispatch system and a vehicle carrying an automated external defibrillator (AED)
Figure 2B:
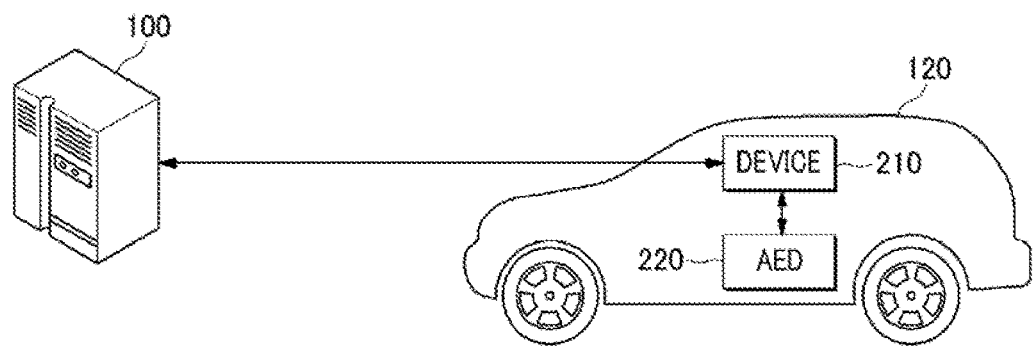
FIG. 2B schematically shows another illustrative example of interaction between an automated external defibrillator (AED) dispatch system and a vehicle carrying an automated external defibrillator (AED)
Figure 2C:
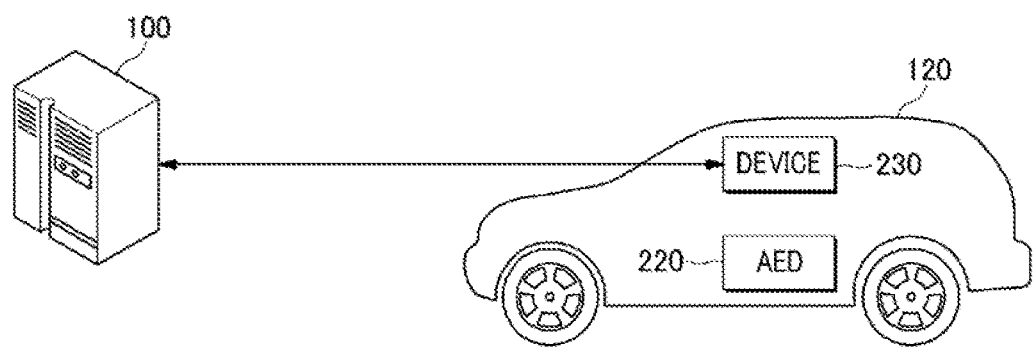
FIG. 2C schematically shows yet another illustrative example of interaction between an automated external defibrillator (AED) dispatch system and a vehicle carrying an automated external defibrillator (AED)

In some embodiments, each of candidate vehicles 120-1, 120-2 and 120-3 may be equipped with an AED (e.g., the vehicle carries an AED that is either temporarily or permanently associated with the vehicle). Each of candidate vehicles 120-1, 120-2 and 120-3 may also include an associated second device (not shown in FIG. 1), configured to communicate with AED dispatch system 100. By way of example, but not limitation, the associated second device may be embedded in the AED of candidate vehicle 120-1, 120-2 or 120-3 (e.g., as illustrated in FIG. 2A). By way of another example, but not limitation, the associated second device may be a portable electronic device associated with candidate vehicle 120-1, 120-2 or 120-3 (e.g., as illustrated in FIGS. 2B and 2C), such as a navigation device, a smartphone, a cellular phone, a tablet computer, or a personal data assistant (PDA).

In some embodiments, the second devices associated with candidate vehicles 120-1, 120-2 and 120-3 may respectively send report messages to AED dispatch system 100. Each report message may be encoded with second location information that may indicate a location of the corresponding one of the second devices, e.g., a location of candidate vehicle 120-1, 120-2 or 120-3. By way of example, but not limitation, each second location information may include a GPS (Global Positioning System) coordinate of the corresponding one of candidate vehicles 120-1, 120-2 and 120-3, cell information of the cellular network accessed by the corresponding one of candidate vehicles 120-1, 120-2 and 120-3, and/or information associated with Wi-Fi access point accessed by the corresponding one of candidate vehicles 120-1, 120-2 and 120-3.

In some embodiments, AED dispatch system 100 may select a vehicle to dispatch from among candidate vehicles 120-1, 120-2 and 120-3 based at least in part on the first location information and the respective second location information. AED dispatch system 100 may take into consideration of which vehicle, among candidate vehicles 120-1, 120-2 and 120-3, is likely to reach patient 105 most rapidly, when selecting the vehicle to be dispatched. In this regard, AED dispatch system 100 may be configured to calculate a distance between patient 105 and each of candidate vehicles 120-1, 120-2 and 120-3 based on the first location information and the respective second location information, and selecting one or more vehicles to be dispatched. Selecting one or more vehicles, for example using a vehicle determination unit, may include determining one or more parameters for each candidate vehicle, such as physical distance from the patient, travel time to the patient, available equipment, medical training of one or more occupants, medical equipment carried by the vehicle, and the like. For example, selecting a vehicle may include selecting a vehicle that is estimated to be closest in distance and/or travel time to patient 105 when AED dispatch system 100 receives the request message. In some examples, a plurality of vehicles may be selected.

In some embodiments, AED dispatch system 100 may select the vehicle to be dispatched further based on direction information of candidate vehicles 120-1, 120-2 and 120-3. By way of example, but not limitation, when the distance between patient 105 and vehicle 120-1 is similar to the distance between patient 105 and vehicle 120-3, AED dispatch system 100 may determine to dispatch vehicle 120-3 since vehicle 120-3 may be moving toward patient 105, while vehicle 120-1 may be moving away from patient 105. In some embodiments, each report message may include the direction information, and AED dispatch system 100 may extract the direction information from each report message. In some other embodiments, AED dispatch system 100 may estimate the direction information based on the second location information.

The report message may be encoded with various information such as the identity of one or more vehicle occupants, vehicle identification (for example, a code number corresponding to the vehicle), medical training level of one or more vehicle occupants, a presence of emergency signaling devices (such as lights and/or sirens), and whether the candidate vehicle is in progress to another medical emergency. The report message may also indicate an estimated travel time to a specific location.

In some examples, a detailed report message may be transmitted at relatively long intervals, while a less detailed report message may be transmitted more frequency such that the real-time location of the vehicle can be readily attained.

In some embodiments, AED dispatch system 100 may be configured to select the vehicle to dispatch based on traffic conditions between patient 105 and candidate vehicles 120-1, 120-2 and 120-3. By way of example, but not limitation, even though the distance between patient 105 and vehicle 120-3 may be estimated as shorter than the distance between patient 105 and vehicle 120-2, AED dispatch system 100 may determine to dispatch vehicle 120-2 when the traffic condition between patient 105 and vehicle 120-3 is estimated as worse than the traffic condition between patient 105 and vehicle 120-2. In some embodiments, AED dispatch system 100 may be configured to receive information about the traffic conditions from one or more traffic watchers.

In some examples, a traffic watcher is a source of traffic information available to a vehicle and/or the AED dispatch system. One or more vehicles may exchange traffic information AED dispatch system. The traffic watcher may be a wireless source of traffic information, for example through radio transmission, other broadcast service, cellular data, wireless network, and the like. The traffic watcher may include automated aspects, human inputs, and the like. For example, an AED dispatch system may receive inputs from a person viewing traffic information, and may use the traffic information as a parameter in selection of one or more vehicles. In some examples, an AED dispatch system may receive traffic information from a traffic watcher, where for example the traffic watcher is a source of traffic information such as an Internet site supplying traffic information, radio transmission, and the like. A traffic watcher may optionally include human input, and may also be a fully automated traffic information source.

In some embodiments, AED dispatch system 100 may be configured to generate an instruction message for the vehicle to be dispatched. The instruction message may be encoded with the first location information and/or route information for the vehicle to be dispatched to reach patient 105. In some embodiments, AED dispatch system 100 may be configured to transmit the generated instruction message to the second device associated with the selected vehicle to be dispatched.

Although FIG. 1 illustrates that AED dispatch system 100 selects the vehicle to be dispatched from among three candidate vehicles 120-1, 120-2 and 120-3, those skilled in the art will appreciate that AED dispatch system 100 may take into consideration of any number of candidate vehicles for possible dispatch of an AED to patient 105.

The first device may be configured to provide a request message. The request message may include first location information that indicates a location of the first device, and therefore may indicate the location of the patient when the patient is in possession of the first device. A request message may include one or more of patient location information, a request for emergency medical assistance at the patient location, patient identity, patient medical records, insurance information, a physical description of the patient, drug prescription information, or any other potentially useful information. An advantage of some examples is that information associated with the patient may be collected by the first device prior to an emergency situation, and thus can rapidly provide such information to medical assisters.

In some embodiments, the request message may include first location information that may indicate a location of the first device, and each of the report messages may include second location information that may indicate a location of the corresponding one of the second devices. The AED dispatch system may then select a vehicle to be dispatched from among the multiple candidate vehicles that are each equipped with the AED, based at least in part on the location of the first device and the locations of the second devices. The AED dispatch system may be configured to select one or more vehicles to dispatch based on consideration of which vehicle, among the multiple candidate vehicles, is able to reach the patient most rapidly. By way of example, but not limitation, the AED dispatch system may be configured to select the vehicle to be dispatched further based on locations of the respective candidate vehicles, and/or traffic conditions between the patient and the respective candidate vehicles.

A second device may be located in a vehicle, or carried, affixed or otherwise associated with the vehicle operator. In some examples, the second device may be similar to that of the first device. The second device may be possessed by the vehicle operator or an occupant of the vehicle. In some examples, the second device may be configured to communicate with vehicle electronics, such as a vehicle navigation system. The second device may be an AED that is adapted for wireless network connectivity. The second device may be configured to transmit a report message that includes second location information to indicate a location of the second device. There may be a plurality of candidate vehicles, where each second device may be associated with one of the plurality of candidate vehicles, and where each candidate vehicle has an automated external defibrillator (AED).

A vehicle may be any type of vehicle including, but not limited to, cars, ambulances, taxis, trucks, motorcycles, buses, two wheeled vehicles (for example, bicycles, motorbikes, scooters), aircraft (such as airplanes, helicopters and the like), boats, and the like. The vehicle may be an official vehicle, such as an emergency vehicle, a police car, an ambulance, a fire vehicle, and the like. An emergency vehicle may use sirens, lights, etc. to arrive at the location quickly. In some examples, the vehicle may be a private vehicle that is associated with one or more defibrillator dispatch services. A vehicle may be adorned with colors and/or logos associated with the AED dispatch system provider.

The second location information may indicate a location of the second device and/or the vehicle with which it is associated. The report messages may be transmitted continuously, at intervals, and/or on request by the AED dispatch system. A second device and an AED dispatch system may be configured for communication over a wireless network such as a phone network, a satellite network, a wireless Internet, or any other appropriate wireless network. The location information may be provided by the second device, or other device that is in communication with the second device.

In some embodiments, responsive to the request message, the AED dispatch system may be configured to generate an instruction message that may include the location of the first device (e.g., the location of the patient), and transmit the generated instruction message to the second device associated with the selected vehicle to be dispatched. By way of example, but not limitation, the instruction message may further include route information for the vehicle to be dispatched to reach the patient.

In some examples, the AED dispatch system may be an automated system. An advantage of some automated system examples is that human-introduced delays may be reduced, increasing the probability of a favorable patient outcome. Some AED dispatch systems may include one or more computer systems arranged in communication with the first and second devices through a network, such as the Internet, phone network, or some other network. Various AED dispatch systems may also be configured to receive data from other sources, such as traffic data, weather data, and the like, and may use such data in calculation of estimated travel times. In some examples, automated AED dispatch systems may be configured to receive a request message, determine location information related to candidate vehicles from report messages, determine one or more selected vehicles to be dispatched to the location corresponding to the request message, and transmit an instruction message to the selected vehicle(s) to proceed to the location associated with the request message, without human intervention. In some examples, this process may be achieved in ten seconds or less, and in some examples in two seconds or less. In some examples, an automated AED dispatch system may include a user interface, configured to receive instructions from a human operator such as override instructions.

FIGS. 2A-2C schematically show illustrative examples of interaction between an automated external defibrillator (AED) dispatch system 100 and a vehicle 120 carrying an automated external defibrillator (AED), arranged in accordance with at least some embodiments described herein. As shown in FIG. 2A, an example AED dispatch system 100 may be configured to interact with a vehicle 120, and an AED 200. As illustrated in FIG. 2B, an example AED dispatch system 100 may be configured to interact with a vehicle 120, an AED 200, and a second device 210. As shown in FIG. 2C, an example AED dispatch system 100 may be configured to interact with a vehicle 120, an AED 220, and a second device 230.

In some example embodiments illustrated in FIG. 2A, AED dispatch system 100 may be arranged to communicate with an automated external defibrillator (AED) 200 carried by vehicle 120. In such cases, AED 200 may be configured to identify its location information, and transmit the identified location information to AED dispatch system 100 in an encoded message (e.g., an instruction message). AED 200 may be further configured to receive the encoded message from AED dispatch system 100. In this example, the AED may also function as the second device, and so a separate second device may not be required.

In some example embodiments illustrated in FIG. 2B, vehicle 120 may be equipped with a device 210 and an AED 220, which may be configured to communicate with each other (e.g., wirelessly, via Bluetooth), and AED dispatch system 100 may be configured to communicate with device 210. In such cases, AED 220 may be configured to identify its location information, and transmit the identified location information to device 210. Second device 210 may be configured to relay or transmit the location information to AED dispatch system 100. Device 210 may be further configured to receive an instruction message from AED dispatch system 100.

In some example embodiments illustrated in FIG. 2C, vehicle 120 may be equipped with a second device 230 and AED 220, and AED dispatch system 100 may be configured to communicate with device 230. In such cases, second device 230 may be configured to identify its location information, and transmit an encoded message to AED dispatch system 100, where the encoded message includes the identified location information and an indication that device 230 is associated with AED 220 (e.g., device 230 and AED 220 are in the same vehicle). Device 230 may be further configured to receive an instruction message from AED dispatch system 100.

By way of example, but not limitation, second device 210 or 230 may be a portable electronic device including, but not limited to, a navigation device, a smartphone, a cellular phone, a tablet computer, or a personal data assistant (PDA). Example second devices may be similar to example first devices.

Figure 3:
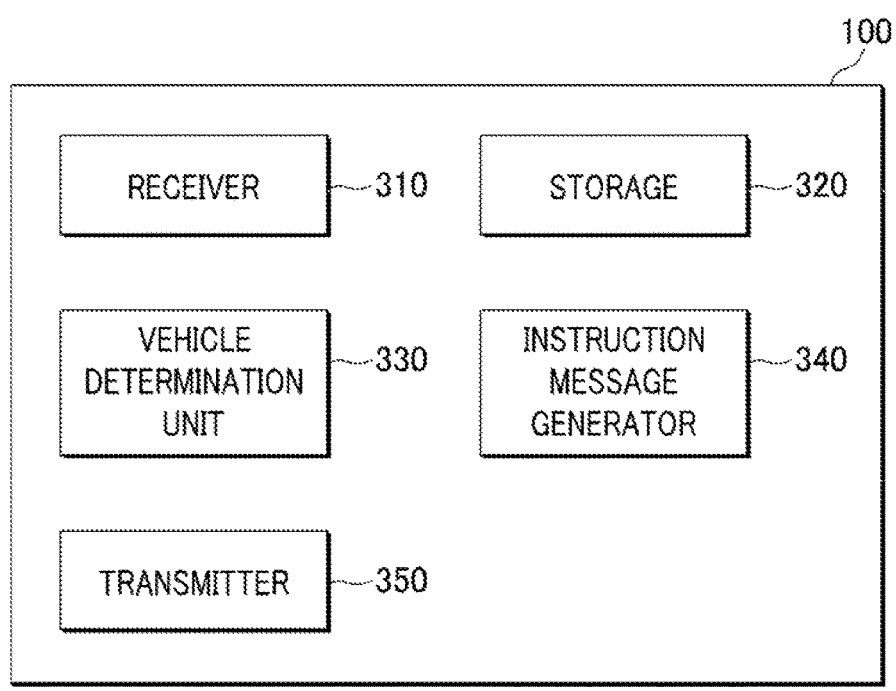
FIG. 3 schematically shows a block diagram of an illustrative example automated external defibrillator (AED) dispatch system.

FIG. 3 schematically shows a block diagram of an illustrative example automated external defibrillator (AED) dispatch system, arranged in accordance with at least some embodiments described herein. As depicted in FIG. 3, the example AED dispatch system 100 includes a receiver 310, storage 320, a vehicle determination unit 330, an instruction message generator 340 and a transmitter 350.

Although illustrated as discrete components, various components may be divided into additional components, combined into fewer components, or eliminated while being contemplated within the scope of the disclosed subject matter. It will be understood by those skilled in the art that each function and/or operation of the components may be implemented, individually and/or collectively, by a wide range of hardware, software, firmware, or virtually any combination thereof. The AED dispatch system components may be provided by one or more server computers and associated components.

Receiver 310 may be configured to receive a request message from a first device (e.g., device 110 in FIG. 1). The request message may be encoded with first location information that may indicate a location of the first device. Receiver 310 may also be configured to receive one or more report messages respectively from one or more of second devices, each of which may be associated with candidate vehicles carrying automated external defibrillators (AEDs) (e.g., candidate vehicles 120-1, 120-2 and 120-3 in FIG. 1). In some examples, an AED may act as the second device. Each report message may be encoded with second location information that may indicate a location of the corresponding one of the second devices. In some embodiments, each report message may further be encoded with direction information of the respective candidate vehicles.

By way of example, but not limitation, the first location information may include coordinates, such as GPS (Global Positioning System) coordinates, of the first device, cell information of a cellular network accessed by the first device, and/or information associated with a Wi-Fi access point accessed by the first device. Also, the second location information may include a GPS coordinate of the corresponding one of the candidate vehicles, cell information of the cellular network accessed by the corresponding one of the candidate vehicles, and/or information associated with a Wi-Fi access point accessed by the corresponding one of the candidate vehicles.

In some embodiments, receiver 310 may be further configured to receive information about traffic conditions from one or more traffic watchers. In some examples, a traffic watcher may be any source of traffic information. A traffic watcher may include an automated (or semi-automated) system configured to collect and broadcast (or otherwise communicate) traffic information to one or more components of the AED dispatch system. Traffic information may include determined and/or estimated traffic conditions such as actual vehicle speeds, delays at certain locations, variable speed limits, meteorological conditions, and the like, for some or all roads in a region served by the AED dispatch system. In some examples, a person may provide input of traffic information to the AED dispatch system, for example by indicating that a particular vehicle should not be selected because of traffic conditions. In some examples, a vehicle may be selected from an adjacent region covered by another AED dispatch system, for example, when advisable due to traffic conditions, increased demand, and the like.

Storage 320 may be configured to store information about the candidate vehicles. In some embodiments, storage 320 may be configured to update information about the candidate vehicles when receiver 310 receives the one or more report messages.

Vehicle determination unit 330 may be configured to select a vehicle to be dispatched from among the candidate vehicles based at least in part on the first location information and the respective second location information. In some embodiments, vehicle determination unit 330 may be configured to select the vehicle for dispatch further based on direction information of the respective candidate vehicles and/or the traffic conditions between the first device and the respective candidate vehicles.

Instruction message generator 340 may be configured to generate an instruction message for the vehicle to be dispatched selected by vehicle determination unit 330. In some embodiments, the instruction message may include the first location information and/or route information for the vehicle to be dispatched to reach the first device. Transmitter 350 may be configured to transmit the instruction message generated by instruction message generator 340 to the vehicle selected by vehicle determination unit 330.

In some examples, the function of the AED dispatch system may be provided by one or more of the first device or the second device. For example, the first device may be configured to operate as the AED dispatch system, and send an instruction message to the second device of the vehicle determined to be dispatched by the first device. In some examples, the second device may be configured to operate as the AED dispatch system on receipt of the request message, for example by comparing the location of the second device acting as the dispatch system with the location of other second devices, and either dispatch its own vehicle or dispatch another vehicle to the location of the first device. First and second devices may also form self-organized networks (e.g., ad hoc networks) to facilitate vehicle dispatch determination.

In some examples, a request message that is encoded with first location information may be received by a receiver of the AED dispatch system. The first location information may also be provided to other emergency systems, such as the 911 emergency network in the United States or equivalent emergency networks in other locations. In response to the request message, the AED dispatch system may capture report messages from one or more second devices. In some examples, the AED dispatch system may be configured to transmit a request for report messages from the second devices, while in other examples the AED dispatch system may passively capture report messages without transmitting the request. The AED dispatch system may be configured to determine one or more candidate vehicles which is able to help the patient. In some examples, an AED dispatch system includes a vehicle determination unit configured to select a candidate vehicle to be dispatched to the patient. The selection of candidate vehicle may be based at least in part on the first location information and the respective second location information, and the selection may be made based on one or more parameters such as travel time to patient, travel distance to patient, medical treatment capability of the vehicle and/or vehicle occupant(s), and/or subscription level of the patient. In some examples, the selection of candidate vehicle may be determined on the basis of an estimated travel time between the first and second locations, and optionally using other information in the report message. The vehicle determination may be made based on one or more report messages, or equivalently from stored information derived therefrom. The AED dispatch system may further include a transmitter configured to transmit an instruction message that includes the first location information to the second device associated with the selected vehicle to be dispatched. On receipt of the instruction message, the one or more selected vehicles may then proceed to the first location. A dispatch system may send one or more messages to the patient after receipt of the request message, such as "Help is on its way." In some examples, a plurality of vehicles are dispatched, and in some examples, once one vehicle of the plurality of vehicles reaches the patient the dispatch instructions for the remaining vehicles may be cancelled.

Figure 4:
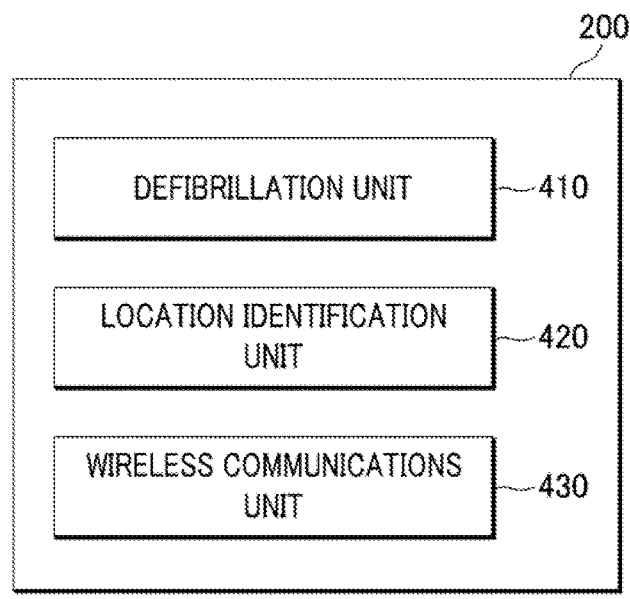
FIG. 4 schematically shows a block diagram of an illustrative example automated external defibrillator (AED)

FIG. 4 schematically shows a block diagram of an illustrative example automated external defibrillator (AED), arranged in accordance with at least some embodiments described herein. As depicted in FIG. 4, the example AED 200 may include a defibrillation unit 410, a location identification unit 420, and/or a wireless communications unit 430.

Although illustrated as discrete components, various components may be divided into additional components, combined into fewer components, or eliminated while being contemplated within the scope of the disclosed subject matter. It will be understood by those skilled in the art that each function and/or operation of the components may be implemented, individually and/or collectively, by a wide range of hardware, software, firmware, or virtually any combination thereof. In some examples, an AED including a wireless communications unit may be configured to operate as the second device, and provide second location information.

Defibrillation unit 410 may be configured to provide a patient (e.g., patient 105 in FIG. 1) with electrical therapy.

Location identification unit 420 may be configured to identify location information of AED 200. By way of example, but not limitation, location identification unit 420 may identify a GPS (Global Positioning System) coordinate of AED 200, cell information of a cellular network accessed by AED 200, and/or a Wi-Fi access point accessed by AED 200.

Wireless communications unit 430 may be configured to transmit, to an associated device, the location information identified by location identification unit 420. In some embodiments, wireless communications unit 430 may be further configured to periodically transmit the identified location information to the associated device.

In some embodiments, the associated device may be a portable electronic device such as a second device. In such cases, wireless communications unit 430 may transmit the identified location information to the associated device via a wireless transmission, such as Bluetooth. In some other embodiments, the associated device may be AED dispatch system 100. In some examples, the automated external defibrillator (AED) may not include the location identification unit and/or the wireless communications unit, these capabilities being provided by a second device.

Example defibrillators which may be used with a defibrillator dispatch system include an automated external defibrillator (AED). An example AED is a device that may be configured to apply electrical therapy to a patient to ameliorate a heart disorder, such as cardiac arrhythmia. The AED may include an electronic circuit, a housing, electrical leads for application of electrical therapy, diagnostic electrodes (which may be the same or different as those used to apply electrical therapy), and the like.

A defibrillator, such as an AED, may be configured to detect and characterize arrhythmia in a patient, for example using sensing and analysis of electrical signals from the patient skin. Application of electrical therapy may be used to induce normal heart function, for example after occurrence of tachycardia (such as ventricular tachycardia) or fibrillation (such as ventricular fibrillation). In some examples, a defibrillator may include an automatic injection system configured to administer a cardiac stimulant drug to the patient, for example in the example of asystole detection.

A defibrillator may also be configured to provide instructions to an operator, using a visual display, voice synthesis, and the like. A defibrillator may also be configured to store patient therapy data related to the patient treatment, for example including therapy data indicative of electrical therapy applied to the patient, and diagnostic data indicative of cardiac function, such as cardiac state before, during, and after electrical therapy administration, and the like.

Figure 5:
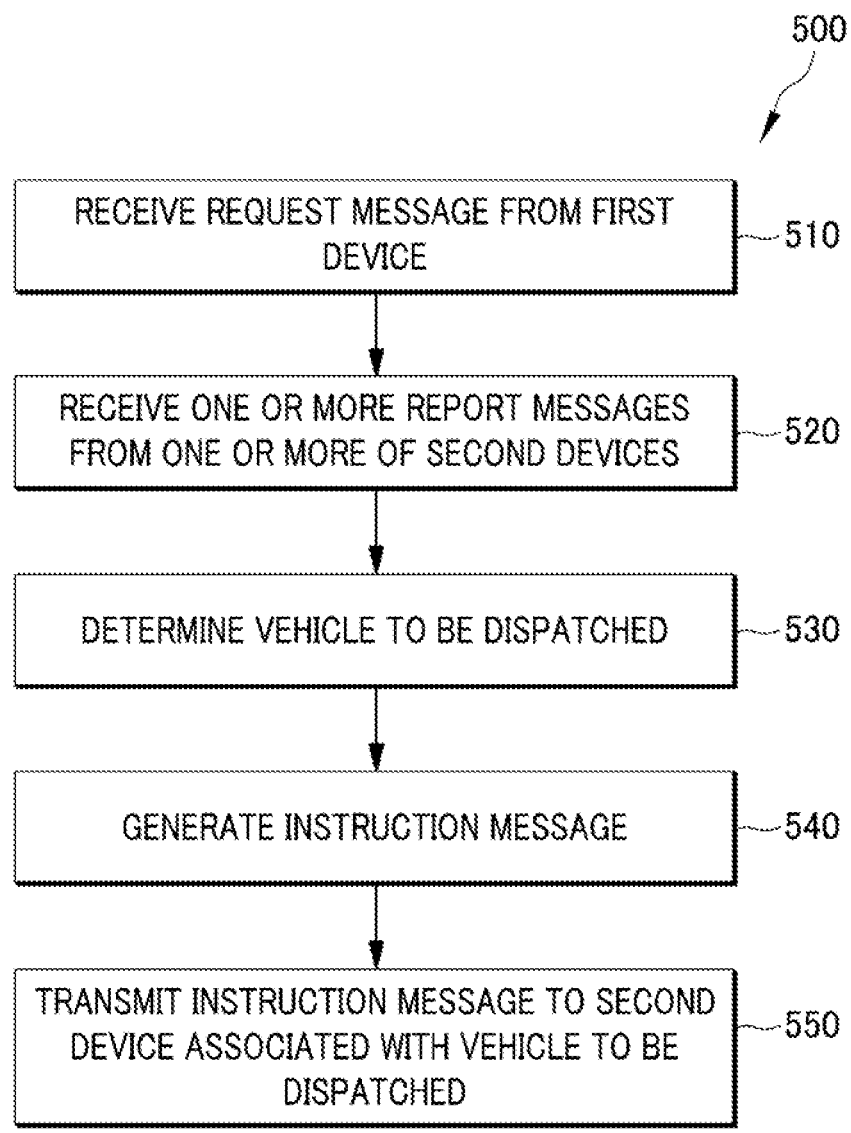
FIG. 5 schematically shows an example flow diagram of a method for an automated external defibrillator (AED) dispatch system.

FIG. 5 schematically shows an example flow diagram of a method for an automated external defibrillator (AED) dispatch system, arranged in accordance with at least some embodiments described herein. An example method shown generally at 500 includes receiving a request message from a first device (block 510), receiving one or more report messages from one or more second devices (block 520), determining the vehicle to be dispatched (block 330), generating an instruction message (block 540), and transmitting the instruction message to a second device associated with the vehicle to be dispatched (block 550).

Method 500 may be implemented in an AED dispatch system such as an AED dispatch system including a receiver, storage, a vehicle determination unit, an instruction message generator, and a transmitter. For example, example method 500 may be performed by an apparatus such as shown in FIG. 3.

Method 500 may include one or more operations, actions, or functions as illustrated by one or more of blocks 510, 520, 530, 540 and/or 550. Although illustrated as discrete blocks, various blocks may be divided into additional blocks, combined into fewer blocks, or eliminated, depending on the desired implementation. In some further examples, the various described blocks may be implemented as a parallel process instead of a sequential process, or as a combination thereof. Method 500 may begin at block 510, "RECEIVE REQUEST MESSAGE FROM FIRST DEVICE."

At block 510, an AED dispatch system (e.g., receiver 310 in FIG. 3) may be adapted to receive a request message from a first device (e.g., device 110 in FIG. 1). The request message may include first location information to indicate a location of the first device. By way of example, but not limitation, the first location information may include a GPS (Global Positioning System) coordinate of the first device, cell information of a cellular network accessed by the first device, and/or information associated with a Wi-Fi access point accessed by the first device. Block 510 may be followed by block 520, "RECEIVE ONE OR MORE REPORT MESSAGES FROM ONE OR MORE OF SECOND DEVICES."

At block 520, the AED dispatch system (e.g., receiver 310) may be adapted to receive one or more report messages from one or more of multiple second devices respectively associated with multiple candidate vehicles carrying automated external defibrillators (AEDs) (e.g., candidate vehicles 120-1, 120-2 and 120-3 in FIG. 1). Each report message may include second location information that may indicate a location of the corresponding one of the second devices. In some embodiments, the AED dispatch system may receive the one or more report messages periodically from the respective second devices. By way of example, but not limitation, the second location information may include a GPS coordinate of the corresponding one of the candidate vehicles, cell information of the cellular network accessed by the corresponding one of the candidate vehicles, and/or information associated with a Wi-Fi access point accessed by the corresponding one of the candidate vehicles. Block 520 may be followed by block 530, "DETERMINE VEHICLE TO BE DISPATCHED."

At block 530, the AED dispatch system (e.g., vehicle determination unit 330 in FIG. 3) may be adapted to determine a vehicle to be dispatched from among the multiple candidate vehicles. In some embodiments, the AED dispatch system may select the vehicle to be dispatched based at least in part on the first location information and the respective second location information. In some embodiments, the AED dispatch system may select the vehicle to be dispatched further based on direction information of the respective candidate vehicles and/or traffic conditions between the first device and the respective candidate vehicles. Block 530 may be followed by block 540, "GENERATE INSTRUCTION MESSAGE."

At block 540, the AED dispatch system (e.g., instruction message generator 340 in FIG. 3) may be adapted to generate an instruction message that may include the first location information. In some embodiments, the AED dispatch system may generate the instruction message to include route information for the vehicle to be dispatched to reach the first device. Block 540 may be followed by block 550, "TRANSMIT INSTRUCTION MESSAGE TO SECOND DEVICE ASSOCIATED WITH VEHICLE TO BE DISPATCHED."

At block 550, the AED dispatch system (e.g., transmitter 350 in FIG. 3) may be adapted to transmit the instruction message to the second device associated with the determined vehicle to be dispatched. In such cases, the vehicle carrying an AED may move to the first location based on the instruction message, thereby delivering electrical therapy to a patient around the first device (e.g., at the first location).

One skilled in the art will appreciate that, for this and other methods disclosed herein, the functions performed in the methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 6:
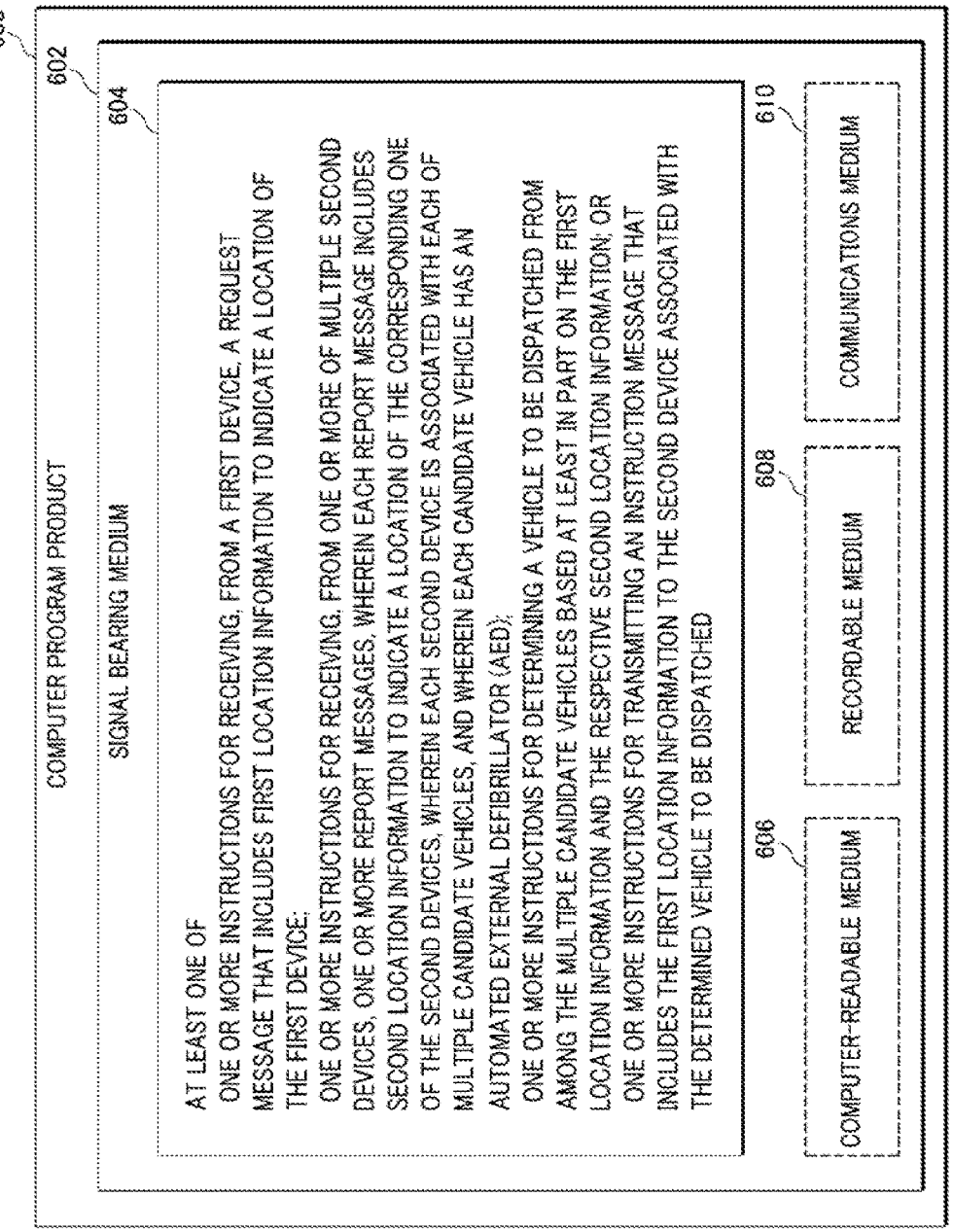
FIG. 6 illustrates an example computer program product that may be utilized to implement dispatch of an automated external defibrillator (AED)

FIG. 6 illustrates an example computer program product 600 that may be utilized to implement dispatch of an automated external defibrillator (AED), arranged in accordance with at least some embodiments described herein. FIG. 6 shows an example computer program product 600 that includes a signal bearing medium 602, instructions stored on the signal bearing medium 602, a computer readable medium 606, a recordable medium 608, and a communications medium 610. The signal bearing medium may be a unitary device, or include several storage media, for example under common computer control.

Signal bearing medium 602 includes one or more instructions 604 that, when executed by, for example, a processor, may provide the functionality described above with respect to FIGS. 1-5.

By way of example, instructions 604 may include: one or more instructions for receiving, from a first device, a request message that includes first location information to indicate a location of the first device; one or more instructions for receiving, from one or more of a plurality of second devices, one or more report messages, wherein each report message includes second location information to indicate a location of the corresponding one of the second devices, wherein each second device is associated with each of a plurality of candidate vehicles, and wherein each candidate vehicle has an automated external defibrillator (AED); one or more instructions for determining a vehicle to be dispatched from among the plurality of candidate vehicles based at least in part on the first location information and the respective second location information; or one or more instructions for transmitting an instruction message that includes the first location information to the second device associated with the determined vehicle to be dispatched. Thus, for example, referring to FIG. 3, an AED dispatch system such as illustrated at 100 may undertake one or more of the blocks shown in FIG. 5 in response to instructions 604.

In some implementations, signal bearing medium 602 may encompass a computer-readable medium 606, such as, but not limited to, a hard disk drive (HDD), a compact disk (CD), a digital versatile disk (DVD), a digital tape, memory, etc. In some implementations, signal bearing medium 602 may encompass a recordable medium 608, such as, but not limited to, memory, read/write (R/W) CDs, R/W DVDs, etc. In some implementations, signal bearing medium 602 may encompass a communications medium 610, such as, but not limited to, a digital and/or an analog communication medium (e.g., a fiber optic cable, a waveguide, a wired communication link, a wireless communication link, etc.). Thus, for example, computer program product 600 may be conveyed to one or more modules of AED dispatch system 100 by an RF signal bearing medium 602, where the signal bearing medium 602 is conveyed by a wireless communications medium 610 (e.g., a wireless communications medium conforming with the IEEE 802.11 standard).

A first device, second device, and an AED dispatch system may each include a computing device. An example computing device is shown in FIG. 7.

FIG. 7 is a block diagram illustrating an example computing device 700, that may be utilized to implement dispatch of an automated external defibrillator (AED), arranged in accordance with at least some embodiments described herein.

In a very basic configuration 702, computing device 700 typically includes one or more processors 704 and a system memory 706. A memory bus 708 may be used for communicating between processor 704 and system memory 706.

Depending on the desired configuration, processor 704 may be of any type including but not limited to a microprocessor (μP), a microcontroller (μC), a digital signal processor (DSP), or any combination thereof. Processor 704 may include one or more levels of caching, such as a level one cache 710 and a level two cache 712, a processor core 714, and registers 716. An example processor core 714 may include an arithmetic logic unit (ALU), a floating point unit (FPU), a digital signal processing core (DSP Core), or any combination thereof. An example memory controller 718 may also be used with processor 704, or in some implementations, memory controller 718 may be an internal part of processor 704.

Depending on the desired configuration, system memory 706 may be of any type including but not limited to volatile memory (such as RAM), non-volatile memory (such as ROM, flash memory, etc.) or any combination thereof. System memory 706 may include an operating system 720, one or more applications 722, and program data 724.

Application 722 may include an AED dispatch algorithm 726 that may be arranged to perform the functions as described herein including the actions described with respect to the AED dispatch system 100 architecture as shown in FIG. 3 or including the actions described with respect to the flow charts shown in FIG. 5. Program data 724 may include any data that may be useful for providing an AED dispatch scheme as is described herein. In some examples, application 722 may be arranged to operate with program data 724 on an operating system 720 such that the AED dispatch scheme as described herein may be provided.

Computing device 700 may have additional features or functionality, and additional interfaces to facilitate communications between basic configuration 702 and any required devices and interfaces. For example, a bus/interface controller 730 may be used to facilitate communications between basic configuration 702 and one or more data storage devices 732 via a storage interface bus 734. Data storage devices 732 may be removable storage devices 736, non-removable storage devices 738, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 706, removable storage devices 736 and non-removable storage devices 738 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 700. Any such computer storage media may be part of computing device 700.

Computing device 700 may also include an interface bus 740 for facilitating communication from various interface devices (e.g., output devices 742, peripheral interfaces 744, and communication devices 746) to basic configuration 702 via bus/interface controller 730. Example output devices 742 include a graphics processing unit 748 and an audio processing unit 750, which may be configured to communicate to various external devices such as a display or speakers via one or more A/V ports 752. Example peripheral interfaces 744 include a serial interface controller 754 or a parallel interface controller 756, which may be configured to communicate with external devices such as input devices (e.g., keyboard, mouse, pen, voice input device, touch input device, etc.) or other peripheral devices (e.g., printer, scanner, etc.) via one or more I/O ports 758. An example communication device 746 includes a network controller 760, which may be arranged to facilitate communications with one or more other computing devices 762 over a network communication link via one or more communication ports 764.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 700 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 700 may also be implemented as a personal computer including both laptop computer and non-laptop computer configurations.

Various examples described herein include methods, systems, and computer architectures configured for prompt delivery of an AED to a patient's location, where the patient may require urgent medical care. AEDs may be provided in various vehicles, such as doctors' private automobiles, public transportation vehicles such as taxis and buses, emergency vehicles, and the like. Information related to vehicle location may be provided using GPS or other positioning system information, which may be provided to a dispatch center effectively continuously, at intervals, and/or on request from the dispatch center.

In some examples, a patient needing an AED may initiate a request message to the AED dispatch center, wherein the request message includes location information such as from a GPS-equipped portable electronic device. One or more suitable candidate vehicles can be identified, based on availability, convenience, travel time to patient, and the like, by the management center and one or more vehicles dispatched to the patient's location, for example with the guidance of GPS.

A patient may be any person that may benefit from the dispatch of the AED, which may not necessarily be a person under the direct care of a medical professional. In some examples, a patient may be a person at risk of heart disease, or a person perceiving themselves at risk, who avails themselves of a defibrillator dispatch service through any suitable arrangement. In various examples, a patient may be a person subscribing to a defibrillator dispatch service. In some other examples, an employer may subscribe an employee to a defibrillator dispatch service, so that the patient is the employee, even though the employee may not consider themselves at risk of heart disease, or be statistically at risk. In various examples, a medical insurance company may include a defibrillator dispatch service incidental to health insurance coverage, in some cases based on a premium paid. In some further examples, the patient may be an outpatient who is provided with a defibrillator dispatch service as part of outpatient service. These above described examples are merely illustrative and not intended to be limiting. For example, the term "patient" may refer to a person that would become a patient under medical care if they were to suffer a heart attack, but are not necessarily under medical care while availing themselves of the potential future benefits of a defibrillator dispatch service. A patient may be any person using or having the option to use a defibrillator dispatch service.

In some examples, an AED dispatch system may locate an AED close to a patient location, and then locate a person (such as a medical profession) close to the AED location, for example using a second device in possession of the person. The AED dispatch system may then instruct the person to retrieve the AED and proceed with the AED to the patient by any convenient approach, for example using a vehicle or on foot. In some examples, the patient may be located in a pedestrianized area (such as an airport terminal, railroad station, retail environment, and the like), and the person may retrieve the AED and convey it to the patient by foot, or using a vehicle appropriate to a pedestrianized area such as an electric cart or the like, or a combination of vehicle and on foot, based upon the patient location. The AED and patient locations may both be within the same pedestrianized area, or within the same group of pedestrianized areas (for example, airport terminal buildings of the same airport).

An advantage of some example defibrillator dispatch systems is that the defibrillator settings may be configured for use on the patient in advance of use of the defibrillator. For example, patient data (such as physiological and/or demographic data) may be obtained from the patient. These data may include weight, height, age, resting heart rate, preexisting medical conditions (such as cardiac abnormalities) genetic data, gender, body mass index, emergency contact information (e.g., name, phone number, email, and/or address of an emergency contact such as a relative), insurance carrier information, known allergies (e.g., to medication, latex, or other material), primary care physician contact information, specialist physician contact information (e.g., cardiologist), organ donor status, presently taken medicine (for example, to avoid administration of incompatible or unfavorably interacting medicine), religious person contact information, and the like. The patient data may be used to determine appropriate defibrillator settings for the patient, for example in terms of electrical parameters used by the defibrillator in relation to electrical therapy, such as voltage, duration, repetition frequency, number of repetitions, applied energy, polarity, and the like. The patient data and/or the determined defibrillator setting data may be associated with the patient, and may be stored so as to be accessible to the defibrillator and/or its operator on use. If a defibrillator is used on the patient, previously determined defibrillator settings may be used or settings appropriate to the previously obtained patient data may be used. The defibrillator may be configured to select appropriate settings based on the patient identity and/or stored patient data, or using stored settings for the patient.

An advantage of some example defibrillator dispatch systems is that defibrillators, such as AEDs, may be located in various locations, and are not limited to medical vehicles such as ambulances. For example, AEDs may be located in any vehicle, such as private vehicles, public transport vehicles, police vehicles, and the like. AEDs may also be located at fixed points in publically accessible locations, such as locations within an airport, railroad station, bus terminal or some other transport facility, office buildings, retail locations, public parks, as well as other publically accessible locations. In some examples, AEDs may be provided at private locations (such as residences, retail locations, private airports, businesses, and the like), for example as part of a subscription service), and dispatched medical personnel may have access to the private location through identity cards, magnetic access cards, transponders, and the like.

An advantage of some example defibrillator dispatch systems is that legal liability for use of a defibrillator on the patient may be reduced or substantially eliminated, for example by prior agreement. For example, liability of the defibrillator operator may be mitigated through one or more contractual terms of subscription to the defibrillator dispatch system, licensing terms related to the purchase, rental, and/or use of the first device, or other agreement incident to join a defibrillator dispatch system or service based thereon.

The present disclosure is not to be limited in terms of the particular embodiments described in this application, which are intended as illustrations of various aspects. Many modifications and variations may be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected," or "operably coupled," to each other to achieve the desired functionality, and any two components capable of being so associated may also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range may be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," and the like include the number recited and refer to ranges which may be subsequently broken down into subranges as discussed above. Finally, as will be understood by one skilled in the art, a range includes each individual member.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. An automated external defibrillator (AED) dispatch system, comprising:
a receiver configured to:
receive a request message from a first device, wherein the request message includes first location information that indicates a location of the first device; and
receive one or more report messages from one or more second devices,
wherein each of the one or more report messages includes second location information that indicates a location of one of the one or more second devices,
wherein each of the one or more second devices is associated with a candidate vehicle from a plurality of candidate vehicles, and
wherein each of the plurality of candidate vehicles has an AED;
a vehicle determination unit, comprising:
a memory implemented in an integrated circuit; and
a processor implemented in an integrated circuit, the processor coupled to the memory, the processor configured to execute an application, which through an AED dispatch algorithm performs:
select two or more candidate vehicles from the plurality of candidate vehicles to be dispatched based on:
the first location information and the second location information,
a subscription level of a patient, the patient associated with the first device, wherein the subscription level identifies a defibrillator dispatch service provided by the AED dispatch system, wherein the subscription level is associated with provision of the AED dispatch system at specific locations, wherein the provision of the AED dispatch system comprises provision of access to one or more users associated with the AED dispatch system, the access being provided based on one or more of an identity card, a magnetic access card, and a transponder, and
direction information associated with the plurality of candidate vehicles extracted from the received one or more report messages, wherein the direction information comprises whether the candidate vehicle is moving towards or moving away from the first device; and
a transmitter configured to:
transmit an instruction message to two or more second devices associated with the selected two or more candidate vehicles to be dispatched, wherein the instruction message includes the first location information and instructions to dispatch the selected two or more candidate vehicles by the two or more second devices.

2. The AED dispatch system of claim 1, wherein information associated with the plurality of candidate vehicles is stored in the memory.

3. The AED dispatch system of claim 1, wherein the receiver is further configured to:
periodically receive the one or more report messages from the one or more second devices; and
update information associated with the plurality of candidate vehicles.

4. The AED dispatch system of claim 1, wherein an instruction message generator is executed by the processor to generate the instruction message for the selected two or more candidate vehicles to be dispatched.

5. The AED dispatch system of claim 4, wherein the instruction message includes route information for the selected two or more candidate vehicles to be dispatched and to reach the first device.

6. The AED dispatch system of claim 1,
wherein the first location information includes a location coordinate of the first device, and
wherein the second location information includes location coordinates of the plurality of candidate vehicles.

7. The AED dispatch system of claim 1,
wherein the first location information includes cell information associated with a cellular network accessed by the first device, and
wherein the second location information includes cell information associated with the cellular network accessed by the plurality of candidate vehicles.

8. The AED dispatch system of claim 1,
wherein the first location information includes information associated with a wireless network access point accessed by the first device, and
wherein the second location information includes information associated with a wireless network accessed by the plurality of candidate vehicles.

9. The AED dispatch system of claim 1, wherein the processor is configured to execute the application, which through the AED dispatch algorithm selects the two or more candidate vehicles from the plurality of candidate vehicles to be dispatched further based on whether the candidate vehicle is in progress to another medical emergency.

10. The AED dispatch system of claim 1, wherein the request message comprises at least one of: a request for emergency medical assistance to the patient at the location of the first device, patient identity, patient medical records, patient insurance information, physical description of the patient, and drug prescription information of the patient.

11. The AED dispatch system of claim 1, wherein the transmitter is further configured to transmit the request message to the two or more second devices associated with the selected two or more candidate vehicles to be dispatched.

12. The AED dispatch system of claim 1, wherein the transmitter is further configured to:
transmit dispatch cancellation instructions, in response to one of the selected two or more candidate vehicles being reached on the first location, to remaining of the two or more second devices associated with remaining of the two or more candidate vehicles.

13. A method performed under control of an automated external defibrillator (AED) dispatch system, the method comprising:
receiving, from a first device, a request message that includes first location information of the first device;
receiving, from one or more second devices, one or more report messages,
wherein each of the one or more report messages includes second location information associated with a location of one of the one or more second devices,
wherein each of the one or more second devices is associated with a candidate vehicle from a plurality of candidate vehicles, and
wherein each of the plurality of candidate vehicles has an AED;
determining two or more candidate vehicles from the plurality of candidate vehicles to be dispatched based on:

the first location information and the second location information, a subscription level of a patient, the patient associated with the first device, wherein the subscription level identifies a defibrillator dispatch service provided by the AED dispatch system, wherein the subscription level is associated with provision of the AED dispatch system at specific locations, wherein the provision of the AED dispatch system comprises provision of access to one or more users associated with the AED dispatch system, the access being provided based on one or more of an identity card, a magnetic access card, and a transponder, and direction information associated with the plurality of candidate vehicles extracted from the received one or more report messages, wherein the direction information comprises whether the candidate vehicle is moving towards or moving away from the first device; and transmitting an instruction message to two or more second devices associated with the determined two or more candidate vehicles to be dispatched, wherein the instruction message includes the first location information and instructions for dispatching the determined two or more candidate vehicles by the two or more second devices.

14. The method of claim 13, further comprising:
receiving information about traffic conditions between the first device and the plurality of candidate vehicles from one or more traffic watchers; and
using the information about the traffic conditions to determine the two or more candidate vehicles to be dispatched.

15. The method of claim 13, further comprising:
generating the instruction message to include route information for the determined two or more candidate vehicles to be dispatched.

16. The method of claim 13,
wherein the first location information includes a coordinate of the first device, and
wherein the second location information includes coordinates of the plurality of candidate vehicles.

17. The method of claim 13, wherein the second device is a portable electronic device.

18. The method of claim 13, wherein determining the two or more candidate vehicles from the plurality of candidate vehicles comprises determining the two or more candidate vehicles to be dispatched based on whether the candidate vehicle is in progress to another medical emergency.

19. The method of claim 13, wherein receiving the request message comprises receiving a request message that comprises at least one of: a request for emergency medical assistance to the patient at the location of the first device, patient identity, patient medical records, patient insurance information, physical description of the patient, and drug prescription information of the patient.

20. The method of claim 13, further comprises transmitting the request message to the two or more second devices associated with the determined two or more candidate vehicles to be dispatched.

21. The method of claim 13, further comprises transmitting dispatch cancellation instructions, in response to one of the determined two or more candidate vehicles reaching the first location, to remaining of the two or more second devices associated with remaining of the two or more candidate vehicles.

* * * * *